United States Patent
Nilsson et al.

[11] Patent Number: 6,162,219
[45] Date of Patent: Dec. 19, 2000

[54] ELECTRODE

[75] Inventors: Eva Nilsson, Sundsvall; Jaak Berendson, Södertälje, both of Sweden

[73] Assignee: Akzo Nobel N.V., Arnhem, Netherlands

[21] Appl. No.: 09/175,967

[22] Filed: Oct. 21, 1998

Related U.S. Application Data

[60] Provisional application No. 60/065,185, Nov. 12, 1997.

[30] Foreign Application Priority Data

Oct. 21, 1997 [EP] European Pat. Off. .............. 97850143

[51] Int. Cl.⁷ ..................................................... A61B 18/14
[52] U.S. Cl. ................................. 606/41; 606/45; 606/49
[58] Field of Search ................................. 606/41, 45, 46, 606/49

[56] References Cited

U.S. PATENT DOCUMENTS

| | | | |
|---|---|---|---|
| 2,447,169 | 8/1948 | Sousa | 606/45 |
| 3,532,095 | 10/1970 | Miller et al. | 606/49 |
| 3,933,616 | 1/1976 | Beer . | |
| 4,074,718 | 2/1978 | Morrison, Jr. | 606/49 |
| 4,677,990 | 7/1987 | Neubauer . | |
| 5,364,393 | 11/1994 | Auth et al. | 606/45 |
| 5,527,451 | 6/1996 | Edwards et al. . | |

FOREIGN PATENT DOCUMENTS

| | | |
|---|---|---|
| 0 038 484 B1 | 12/1983 | European Pat. Off. . |
| 0 316 995 A1 | 5/1989 | European Pat. Off. . |
| 0 356 009 A1 | 2/1990 | European Pat. Off. . |
| 0 574 904 A1 | 12/1993 | European Pat. Off. . |
| 345 396 | 5/1972 | Sweden . |
| 345 970 | 6/1972 | Sweden . |
| 349 952 | 10/1972 | Sweden . |
| 1147442 | 4/1969 | United Kingdom . |
| WO 92/02272 | 2/1992 | WIPO . |
| WO 95/10978 | 4/1995 | WIPO . |

OTHER PUBLICATIONS

Brunelle et al, "A Bipolar Electrode for Vascular Electro-coagulation with Alternatin Current", Radiology, vol. 137, No. 1, ps 239–240, Oct. 1980.

Reidenbach et al, A new method for the endoscopic coagulation of mucous membrane lesions using high frequency electric currents, Biomed. techn. 23, ps 71–74, Apr. 1978.

*Primary Examiner*—Lee Cohen
*Attorney, Agent, or Firm*—Burns, Doane, Swecker & Mathis, L.L.P.

[57] ABSTRACT

The present invention is related to an electrode for destruction of biological tissue, suitably tumor tissue such as cancer. Prior art electrodes suffers from several disadvantages, such as e.g. a non-uniform current distribution, resulting in a oval and unpredictable destruction zone in the tissue. The present invention provides an electrode for destruction of biological tissue, comprising an electrical conductor (2) with a first thickness ($t_1$), provided with electrical insulation (3) having a second thickness ($t_2$), the conductor being connected to a current source at one end and electrically connected to an electrode head (4) at the other end of the conductor, where the electrode head serves for supplying current to the zone of the biological tissue, wherein the electrode head (4) is substantially spherical (5,10) with a diameter (D), where said diameter of the sphere is equal to or larger than said first thickness ($t_1$). The advantage with the electrode of the present invention is above all the creation of a substantially symmetrical circular destruction zone.

19 Claims, 1 Drawing Sheet

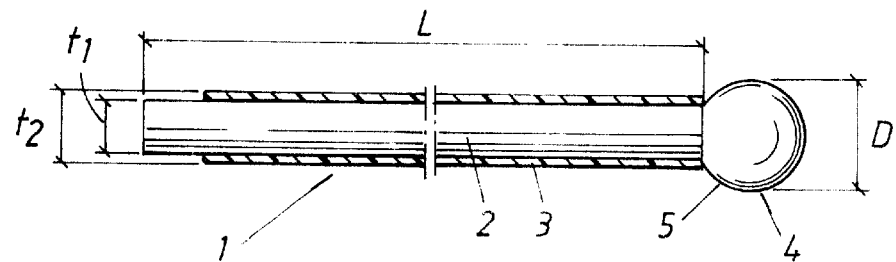
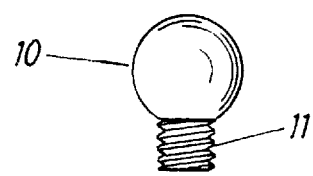
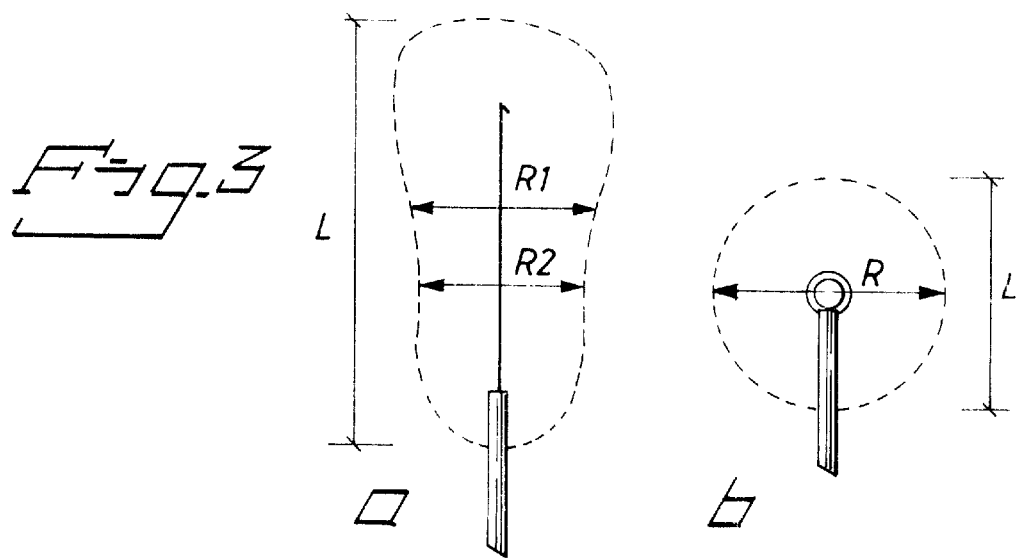

ELECTRODE

This application claims benefit to provisional Application No. 60/065,185 filed Nov. 12, 1997.

BACKGROUND OF THE INVENTION

The present invention is related to an electrode for destruction of biological tissue, suitably tumour tissue such as cancer. The tip, or head, of the electrode is substantially spherical in order to obtain a symmetrical circular destruction zone.

One way of treatment of biological tissue is electrochemical treatment of cancer (ECT), which is a rather undeveloped method to eliminate biological tissue. Greater understanding of the mechanisms of electrochemical treatment is needed for the method to get recognised. The development of ECT as a clinically acceptable therapy has been hindered by uncertainties regarding the mechanism of tissue destruction and the parameters that are important in the process. To be able to understand the mechanism behind ECT, and to develop an effective dosage method, a Swedish interdisciplinary research group, was formed in 1993.

In electrochemical treatment of cancer (ECT), the biological tissue is treated with a direct current. The anode is preferably placed in the biological tissue and the cathode is placed in a blood vessel or in fresh surrounding tissue. When using platinum electrodes, the main reactions are decomposition of water along with oxidation and reduction of substances dissolved in tissue. Consequently, the evolution of oxygen, as well as acidification and formation of chlorine, take place at the anode:

$$2H_2O \leftrightarrows O_2 + 4H^+ + 4e^- \quad (1)$$

$$2Cl^- \leftrightarrows Cl_2 + 2e^- \quad (2)$$

At the cathode, water is decomposed into hydrogen and hydroxyl ions:

$$2H_2O + 2e^- \leftrightarrows H_2 + 2OH^- \quad (3)$$

The ionic species produced at the anode and cathode are transported to the surrounding tissue, mainly by means of diffusion and migration. pH values down to 1 are usually obtained in the tissue close to the anode and a pH of about 12 can be measured at the cathode. Due to the formation of acid and base hematin, the affected tissue becomes dark brown. During electrolysis, the current density may usually be about $10^{-2}$–$10^{-1}$ A/cm$^2$ and the voltage between the anode and cathode can be about 5–15 V. The toxic and destroying action of ECT is assumed to be due to a strong acidification of a zone around the anode, chlorination of tissue constituents close to the anode, electrocoagulation and other possible effects caused by the electric field.

The relatively high current density used for ECT-electrodes, is a prerequisite in order to maintain the oxygen evolution and the acidification around the anode. For this reason, the electrode material and geometry are crucial elements in ECT treatment. For instance, electrodes made of stainless steel would not be suitable for maintaining the oxygen evolution and the acidification around the anode. With respect to the geometry, a needle shaped and tapered head of the electrode causes a non-uniform current distribution, resulting in a oval and unpredictable destruction zone in the tissue.

Endocardiac electrodes, constructed for stimulation of the heart or other muscles, cannot be used for destruction of biological tissue. Endocardiac electrodes uses pulsed current with a low current density. Initially, the current density can be about $10^{-3}$ A/cm$^2$, but is quickly transferred to about $10^{-5}$ A/cm$^2$. If the purpose of the endocardial treatment is just to gently stimulate nerves of a certain type of tissue, the current density will be as low as in the range of $10^{-5}$ A/cm$^2$ down to $10^{-7}$ A/cm$^2$. Besides, the shape and the material of endocardiac electrodes are different compared to electrodes for biological tissue destruction. Moreover, mechanical stability of wire electrodes is often poor due to the tapered end and the overall construction, which implies that wire electrodes only can be used a few times.

U.S. Pat. No. 4,677,990 relates to an endocardial electrode having a flexible electrical conductor, which can assume arbitrary curvatures or contours.

EP-B1-0038484 discloses an endocardial electrode arrangement for the intracardial stimulation of the heart. The electrode comprises a plurality of loops of soft material and are fastened to the electrode head. The aim is to fix electrode to the heart wall.

EP-A-316995 relates to an electrode for treatment of body tissue. The electrode is formed by a platinum wire which is passed through a tube of insulating material. The head of the electrode is formed by winding the end of the wire.

The aim with the ECT treatment is to get a uniform, symmetrical and reproducible destruction zone. This aim is met by the electrode of the present invention.

According to the present invention, the above mentioned problems have been solved by providing an electrode for destruction of biological tissue, comprising an electrical conductor with a first thickness, provided with electrical insulation having a second thickness, the conductor being connected to a current source at one end and electrically connected to an electrode head at the other end of the conductor, where the electrode head serves for supplying current to the zone of the biological tissue, wherein the electrode head is substantially spherical with a diameter, where said diameter of the sphere is equal to or larger than said first thickness.

The advantage with the electrode of the present invention is above all the creation of a substantially symmetrical circular destruction zone. This is due to the possibility to create a uniform current distribution with the spherical head of the electrode according to the present invention. One great advantage is the predictability of the destruction area. Further, the mechanical stability of the present new electrode is superior to conventional electrodes and this allows for the electrode to be used in many treatments before it has to be discarded. Besides, this new construction of electrodes opens the possibility for a wide range of applicable embodiments.

BRIEF DESCRIPTION OF THE DRAWINGS

FIG. 1 illustrates a cross-sectional view of an electrode with a spherical head for the treatment of biological tissue, according to one aspect of the present invention;

FIG. 2 illustrates a side view of a spherical exchangeable electrode head, according to one aspect of the present invention; and FIGS. 3a and 3b illustrate a wire electrode and a spherical electrode, respectively, according to aspects of the present invention.

DETAILED DESCRIPTION OF THE PREFERRED EMBODIMENTS

According to the present invention, the electrode head has perferably the shape of substantially a smooth and regular sphere, globe or ball, with a certain diameter. It is important that the diameter of the sphere is equal to or larger than the thickness of the electrical conductor in order to give a uniform current distribution resulting in a symmetrical destruction zone in the biological tissue. Preferably, the diameter of the sphere is larger than the thickness of the electrical conductor. This is due to the fact that an electrical conductor with a thickness larger than the electrode head, or sphere, could act as a shield for the current at the treatment. However, the outer diameter of the electrical insulation coating of the electrical conductor may be the same thickness as the diameter of the spherical head, but preferably the thickness of the conductor incorporating the insulation coating is less than the diameter of the sphere. The electrical insulation can be fluoroplastics such as PTFE, PVDF, PFA, FEP, Teflon®, or other suitable plastic material, or the similar. The sphere has suitably a diameter in the range of from about 0.1 mm up to about 5 mm, preferably in the range from about 0.5 mm up to about 3 mm and more preferably in the range from about 0.75 mm up to about 1.5 mm. Although the sphere is substantially spherical, the sphere could be slightly flattened at the so called poles. The thickness of the conductor, preferably also incorporating the thickness of the electrode insulation, is smaller than the diameter of the sphere. The thickness of the conductor can be in the range of from about 0.05 mm up to about 4.5 mm but always slightly smaller than diameter of the spherical electrode head. Suitably the thickness of the conductor is in the range of from about 0.2 mm up to about 2.0 mm and preferably in the range of from about 0.5 mm up to about 1 mm.

In contrast to the pulsed current used in conventional endocardial wire electrodes, the electrode of the present invention preferably uses a constant direct current (DC), i.e. a direct current without substantial variation (in contrast to a pulsed current). The current density applied with the electrode of the present invention is suitably in the range of from about $10^{-4}$ A/cm$^2$ up to about 1 A/cm$^2$, preferably in the range of from about $10^{-4}$ A/cm$^2$ up to about $5 \cdot 10^{-1}$ A/cm$^2$ and more preferably in the range of from about $10^{-3}$ A/cm$^2$ up to about $5 \cdot 10^{-1}$ A/cm$^2$. The electrode according to the present invention can be connected to a DC source so it serves as an anode. Consequently, the electrode connected to a DC source, can operate with a current density in the range of from about $10^{-4}$ A/cm$^2$ up to about $5 \cdot 10^{-1}$ A/cm$^2$.

The total length of the electrode is suitably less than about 500 mm, but suitably exceeding about 100 mm. The length is preferably in the range from about 150 mm up to about 250 mm. At the opposite end of the electrode compared to the electrode head, the electrode is connected to a current source (power supply).

When the electrode is acting as an anode, one or more noble metals alone or in any mixture can be used. Use is suitably made of titanium, tantalum, zirconium or niobium, as base material for the anode, but then provided with a coating. Preferably rhodium, palladium, platinum or iridium, or mixtures thereof, is used as material for the anode, as base material, but also as the sole material. The surface of the anode can be coated with a layer of an electrocatalytic active and/or selective material. Suitable materials for the layer are for example, noble metal oxides or platinum, but also other oxides such as e.g. tin oxide are of interest depending on the desired reaction on the anode. As examples of such coating on titanium, mention is made of precious metal oxides or mixtures thereof which are stated in Swedish Patents 345,396, 345,970 and 349,952, or other coatings based on oxides or metals. Suitable coatings on a titanium anode can be Pt, TiO$_2$+RuO$_2$, TiO$_2$+IrO$_2$, or mixtures thereof, or other noble metal oxides. In addition, the anode can be coated with graphite, diamond or other higher coal compounds in various structures. With respect to e.g. diamond, the coating can be applied by the CVD-method (Chemical Vapour Deposition) and doped with boron or other suitable materials. Also magnetite (Fe$_3$O$_4$) could be possible as anode coating.

The spherical head, or the electrical conductor, or even the whole anode may be provided with the aforementioned materials. Suitably only the spherical head of the anode can be made of coated titanium, platinum, rhodium, palladium or noble metal oxides, while the electrical conductor can be made of titanium solely. Preferably the electrical conductor is made of titanium and a spherical head of the anode made of platinum, is welded to the titanium conductor.

When the electrode is acting as a cathode, platinum, iridium or alloys of them, are suitable materials for the cathode.

According to an embodiment of the present invention the spherical head of the electrode can be a separate part of the electrode, which thus can be exchangeable. A spherical head of an electrode may be welded to the end of an electrical conductor. Suitably the sphere is provided with a threaded socket, which implies that the sphere easily can be exchanged. In this way, sphere's can be made in various materials, or coated with various alloys, and be used for different selective treatments of biological tissue in order to reach a desired effect.

In another embodiment, the electrode can be provided with internal channels for supplying salt solution to the area of the tissue which are to be treated. The electrical conductor and the spherical end of the electrode, can e.g. be provided with one or more internal channels. The sphere is suitably provided with several channels, which emerge on evenly spreaded spots around the surface of the sphere. The salt solution can be a physiological saline solution.

According to yet another embodiment, the spherical head of the electrode may comprise of several thin threads which are forced to form a pseudo-spherical head. Such thin threads can initially be arranged parallel to the extension of the electrical conductor and each end of the threads respectively, can be secured to the outmost end of the conductor, i.e. the tip of the electrode. The other ends of said threads are free to move relative the body of the electrical conductor. Consequently, the movable free ends of the threads can be attached e.g. to the bottom of an outer tubing or the similar, surrounding the electrical conductor and arranged a short distance from the tip of the electrical conductor. Said outer tubing can be affected by some means in the direction of the tip of the electrical conductor, where said thin threads are firmly secured, leading to the formation of a spherical head erected by several thin threads. In this way, a spheroid or ellipsoid electro-geometry can be achieved. When the electrode initially is stuck in the body, the thin threads are preferably arranged along the electrode conductor according to the embodiment of the invention, which may be advantageous in order to get the smallest possible influence of the body tissue. When the electrode is fixed in the desired area to be treated, said outer tubing is influenced to affect the threads to form a shape of a spherical head. Suitably this so-called pseudo-sphere may comprise of at least from about 2 threads, more suitably from about 4 threads and preferably from about 8 up to about 16 threads. The thin threads have a thickness smaller than the electrical conductor.

The present invention also relates to a method for carrying out a medical treatment of biological tissue, suitably a tumour, with an ECT-electrode as disclosed. Thus, use is made of an electrode, having a substantially spherical electrode head with a diameter, which is larger or equal to the thickness of the electrical conductor of said electrode. According to the method, at least one first electrode comprising an electrode head (4) and an electrical conductor (2) is inserted in a body and fixed in a desired area of said tissue, at least one second electrode electrically connected to said first electrode, said electrical conductor (2) of the first electrode with a first thickness ($t_1$), provided with an electrical insulation (3) having a second thickness ($t_2$), said conductor being connected to a current source at one end and electrically connected to the electrode head (4) at the other end of the conductor, where the electrode head serves for supplying current to the zone of the biological tissue, where the electrode head (4) is substantially spherical (5,10) with a diameter (D), where said diameter of the sphere is equal to or larger than said first thickness ($t_1$). Said first electrode can serve as anode or cathode. Said second electrode is preferably inserted and fixed at a suitable distance from the anode. A direct current density, suitably in the range of from about $10^{-4}$ A/cm$^2$ up to about 1 A/cm$^2$, is preferably passed between the electrodes by means of a constant-current power supply. The treatment time is suitably chosen with respect to the desired result and specific tissue.

The invention will now be described in more detail with reference to the accompanying drawings. However, the invention is not restricted to the embodiments illustrated, but many other variants are feasible within the scope of the claims.

A preferred embodiment of the invention will be described below with reference to the accompanying drawing in which: FIG. 1 illustrates in cross-section an electrode with a spherical head for treatment of biological tissue according to the present invention. FIG. 2 demonstrates a side view of a spherical exchangeable electrode head according to an embodiment of the present invention. FIG. 3 shows a wire electrode (3a) and a spherical electrode (3b), which have been compared in the example below.

FIG. 1 shows according to the present invention an electrode (1) for destruction of biological tissue, comprising an electrical conductor (2), having a thickness ($t_1$), the electrode being provided with electrical insulation (3), having a thickness ($t_2$). The electrical conductor being connected to a current source at one end and electrically connected to an electrode head (4) at the other end of the conductor. The electrode head (4) has the shape of a sphere (5) with a diameter (D). Said diameter of the sphere is larger than said thickness ($t_1$).

FIG. 2 illustrates an ECT-electrode according to an embodiment of the present invention with a spherical head (10), provided with a threaded socket (11). The sphere can be unscrewed and exchanged to another spherical head, possibly comprising a different material or design.

EXAMPLE

All procedures to be described complied with the "Djurförsöksetiska Nämndens" of Sweden (a governmental institution), decision: C112/96. Four female adult CD rats bred by Charles River, Sweden, at a weight of about 350 g were used in the experiment. Anaesthesia was administered by injection of Dormicum®/Hypnorm® intraperitoneally. Two electrode geometries (see FIG. 3), wire (FIG. 3a) and sphere (FIG. 3b), both made by Pt:Ir (9:1), were used in the experiment. Two rats were treated using wire electrodes and two rats were treated using spherical electrodes. The active part of the wire electrodes (FIG. 3a) had a length of 15 mm and a diameter of 0.2 mm. The rest of the wire surface was insulated by using Teflon®. 1 mm hooks were made in the tips of the electrodes in order to fix the electrodes in the tissue. The spherical electrodes (FIG. 3b) had a diameter of 1 mm. The spheres were merged to Pt:Ir (9:1) sticks with a diameter of 0.5 mm. The sticks were electrically insulated using Teflon®. The anode was fixed in the fourth mammary gland on the right side (dx 4), guided by a permanent catheter. The cathode was fixed in the same manner in the fourth mammary gland on the left side (sin 4). The electrodes were placed in parallel with the length of the rat. The distance between the electrodes was varied between 52–65 mm. A direct current of $5 \cdot 10^{-3}$ A was passed between the electrodes by means of a constant-current power supply. Linear current ramps were used at the start of the treatment and at the end to avoid muscle twitching. The length of these ramps were 2 minutes. The total treatment time was 52 minutes and consequently the total charge passed between the electrodes was 15 Coulomb. The voltage between the anode and cathode was continuously monitored and was normally about 6–10 V. After the electrolysis the rat was eustanised by injection of pentothal natrium® intra cardially. The macroscopic dark brown coloured destruction zones were then measured. The anodic and cathodic destruction zones were measured from above, through the skin (as shown in FIG. 3). The measured radiuses R1 and R2 were situated 5 mm from the respective tip of the wire electrode. The characteristic dimensions, R1, R2 and L in the wire case (FIG. 3a), and R and L in the spherical case (FIG. 3b), of the anodic and cathodic destruction zones are listed in Tables 1 and 2 below. It has to be emphasized that the mammary tissue in rat is not spherical but quite flat with a depth of about 5 mm. Therefore, the destruction zone is also shaped more like a disc with about the same depth.

TABLE 1

| Rat No. | Size of anodic destruction zone [mm] | | | Size of cathodic destruction zone [mm] | | |
| --- | --- | --- | --- | --- | --- | --- |
| | R1 | R2 | L | R1 | R2 | L |
| 1 | 8 | 6 | 18 | 6 | 9 | 17 |
| 2 | 6 | 6 | 19 | 6 | 12 | 22 |

Table 1 shows measured sizes of the macroscopic destruction zone, using wire electrodes. As evident from the results presented, the radiuses (R1 and R2) are about half, to one third, of the length (L) of the destruction zone, which then could be characterised as oval shaped. Besides, the oval is unevenly, irregular shaped.

TABLE 2

| Rat No. | Size of anodic destruction zone [mm] | | Size of cathodic destruction zone [mm] | |
| --- | --- | --- | --- | --- |
| | R | L | R | L |
| 3 | 8 | 10 | 12 | 13 |
| 4 | 11 | 12 | 13 | 14 |

Table 2 shows measured sizes of the macroscopic destruction zone, using spherical electrodes. As evident, the radius (R) and the length (L) almost correlates. Hence, the destruction zone is almost circular.

When using wire electrodes, the destruction zones were shaped as irregular ovals and the tissue destruction was not reproducible at the cathode. One reason for this irregular geometry is the non-uniform current distribution on the wire electrodes. The current density may be somewhat centred close to the tips of the electrode, due to the so-called edge effect, since the uptake area for the current is larger at a tip or an edge compared to a planar surface. Another reason for these irregularities may be that the wire electrodes are very thin and flabby and are therefore quite hard to apply with good precision. They may also move during the experiment as a result of muscle twitching. In the case of spherical electrodes, the electrode were easy to apply, due to the robust design, and the destruction zones were practically circular.

What is claimed is:

1. An electrode connected to a direct current source for destruction of biological tissue, said electrode comprising an electrode head and an electrical conductor, said electrical conductor having a first thickness ($t_1$) and electrical insulation being provided on said electrical conductor, said conductor being connected to the direct current source supplying direct current at one end and electrically connected to the electrode head at the other end of the conductor, wherein the electrode head provides a current density ranging from 0.0001 to 1 A/cm$^2$ and is substantially spherical with a diameter equal to or larger than said first thickness ($t_1$).

2. An electrode according to claim 1, wherein said diameter of the electrode head is larger than said first thickness ($t_1$).

3. An electrode according to claim 1, wherein the electrode head has a diameter in the range of from about 0.5 mm up to about 3 mm, and the thickness ($t_1$) of the conductor is in the range of from about 0.2 mm up to about 2.0 mm, wherein said thickness ($t_1$) is smaller than the diameter of the spherical electrode head.

4. An electrode according to claim 1, wherein at least the spherical head of the electrode is made of platinum or iridium, or mixtures thereof.

5. An electrode according to claim 1, wherein the electrode head is exchangeable and provided with a threaded socket.

6. An electrode according to claim 1, wherein the electrode is provided with internal channels for supplying salt solution to the area of the tissue which is to be treated.

7. An electrode connected to a direct current source for destruction of biological tissue, said electrode comprising an electrode head and an electrical conductor, said electrical conductor having a first thickness ($t_1$) and electrical insulation being provided on said electrical conductor, said conductor being connected to the direct current source supplying direct current at one end and electrically connected to the electrode head at the other end of the conductor, wherein the electrode head provides a current density ranging from 0.0001 to 1 A/cm$^2$ and is substantially spherical with a diameter equal to or larger than said first thickness ($t_1$), wherein said electrode head is coated with at least one material selected from the group consisting of noble metal oxides, Pt, tin oxide, precious metal oxides, $TiO_2+RuO_2$, $TiO_2+IrO_2$, graphite, diamond, higher coal compounds, and $Fe_3O_4$.

8. A method according to claim 7, wherein said diameter of the electrode head is larger than said first thickness ($t_1$).

9. A method according to claim 7, wherein said first electrode serves as an anode.

10. A method according to claim 7, wherein said first electrode serves as a cathode.

11. A method for carrying out a medical treatment of biological tissue, comprising:

(a) inserting at least one first electrode into a body and fixing said first electrode in a desired area of said tissue, said first electrode comprising an electrode head and an electrical conductor, and said first electrode being connected to a direct current source, (b) electrically connecting at least one second electrode to said first electrode, and (c) applying current density between said electrodes such that current is supplied to said tissue by said electrode head so as to produce a substantially symmetrical circular destruction zone, wherein said electrical conductor of the first electrode has a first thickness ($t_1$), an electrical insulation being provided on said electrical conductor, said conductor being connected to the direct current source providing direct current at one end and electrically connected to the electrode head at the other end of the conductor, wherein the electrode head is substantially spherical with a diameter equal to or larger than said first thickness ($t_1$).

12. A method according to claim 11, wherein a current density in the range of from about $10^{-4}$ A/cm$^2$ up to about 1 A/cm$^2$ is applied between the electrodes.

13. A method according to claim 12, wherein a current density in the range of from about $10^{-4}$ A/cm$^2$ up to about $5 \cdot 10^{-1}$ A/cm$^2$ is applied between the electrodes.

14. A method according to claim 11, wherein a constant direct current is applied between the electrodes.

15. A method according to claim 11, wherein the electrode head has diameter in the range of from about 0.5 mm up to about 3 mm, and the thickness ($t_1$) of the conductor is in the range of from about 0.2 mm up to about 2.0 mm, wherein said thickness ($t_1$) is smaller than the diameter of the spherical electrode head.

16. A method according to claim 11, wherein at least the spherical head of the electrode is made of platinum or iridium, or mixtures thereof.

17. A method according to claim 11, wherein the electrode head is exchangeable and provided with a threaded socket.

18. A method according to claim 11, wherein the electrode is provided with internal channels for supplying salt solution to the area of the tissue which is to be treated.

19. A method according to claim 11, wherein the electrodes are connected to a DC source to operate with a current density in the range of from about $10^{-4}$ A/cm$^2$ up to about $5 \cdot 10^{-1}$ A/cm$^2$.

* * * * *